(12) United States Patent
Kral et al.

(10) Patent No.: US 6,582,654 B1
(45) Date of Patent: Jun. 24, 2003

(54) FLUID SPRAY SYSTEM FOR CLEANING AND STERILIZING MEDICAL DEVICES SUPPORTED ON A RACK

(75) Inventors: Jude A. Kral, Twinsburg, OH (US); Robert M. Priest, Eastlake, OH (US); Daniel N. Kelsch, Fairview Park, OH (US); James C. Hlebovy, Chardon, OH (US); Bill R. Sanford, Willoughby, OH (US); Alan J. Greszler, Elyria, OH (US); Francis John Zelina, Lake City, PA (US); Kenneth J. Klobusnik, Lake City, PA (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/498,869

(22) Filed: Feb. 7, 2000

(51) Int. Cl.[7] ................................................ A61L 2/18
(52) U.S. Cl. .................... 422/28; 422/292; 422/297; 422/300; 134/161; 134/170; 134/171; 134/200
(58) Field of Search .................... 422/28, 105, 292, 422/300, 297; 134/95, 161, 170, 171

(56) References Cited

U.S. PATENT DOCUMENTS

| | | | |
|---|---|---|---|
| 1,540,793 A | 2/1925 | Maloney | |
| 3,893,843 A | 7/1975 | Fry et al. | 134/10 |
| 4,142,539 A | 3/1979 | Shih et al. | 134/113 |
| 4,278,101 A | 7/1981 | Tanaka et al. | 134/167 C |
| 4,281,674 A * | 8/1981 | Tanaka et al. | 134/95 |
| 4,489,741 A | 12/1984 | Ogasawara | 134/179 |
| 4,552,728 A * | 11/1985 | Taylor | 422/300 |
| 4,731,222 A | 3/1988 | Kralovic et al. | 422/37 |
| 4,892,706 A | 1/1990 | Kralovic et al. | 422/28 |
| 4,928,917 A * | 5/1990 | Wolf | 248/507 |
| 5,027,840 A | 7/1991 | Nezworski | 134/57 |
| 5,035,752 A | 7/1991 | Tanaka et al. | 134/32 |
| 5,077,008 A | 12/1991 | Kralovic et al. | 422/37 |

(List continued on next page.)

Primary Examiner—Robert J. Warden, Sr.
Assistant Examiner—Sean E. Conley
(74) Attorney, Agent, or Firm—Fay, Sharpe, Fagan, Minnich & McKee, LLP (57) ABSTRACT

A fluid delivery system (20) for an automated processor (A) includes spray nozzles (102, 104, 106, 108, 110) for sequentially spraying washing, microbial decontaminant and rinsing solutions over a lumened device (B), such as an endoscope. The fluid delivery system also includes connection ports (150, 152, 154) for connecting with internal passages (187) of the device to deliver the washing and microbial decontaminant solutions thereto. A removable rack (21), specially configured for the particular device, positions the device within a chamber (12). The spray nozzles are located on rear and side walls (114, 116, 118) and on a door (18) of the chamber, such that the device is impinged with spray from all directions. Sets (102, 104) of the spray nozzles are pulsed in sequence so that the spray jets (122) do not cancel each other out. Leaking connectors (184) connect the automated processor connection ports with inlet ports (196) of the device and allow a portion of the cleaning, decontaminant, and rinsing solutions to leak from each inlet port. A computer control system (80) controls cleaning, decontamination, rinsing, and drying stages of a cycle, which are all carried out within the chamber, obviating the need for human contact with the device during processing.

28 Claims, 8 Drawing Sheets

U.S. PATENT DOCUMENTS

| | | | |
|---|---|---|---|
| 5,090,433 A | | 2/1992 | Kamaga ................. 134/169 C |
| 5,091,345 A | | 2/1992 | Becker ........................ 501/14 |
| 5,120,512 A | | 6/1992 | Masuda ...................... 422/297 |
| 5,125,981 A | * | 6/1992 | Belanger et al. .............. 134/18 |
| 5,225,160 A | * | 7/1993 | Sanford et al. ............... 422/28 |
| 5,279,799 A | * | 1/1994 | Moser ........................ 422/292 |
| 5,288,467 A | | 2/1994 | Biermaier ................... 422/116 |
| 5,310,524 A | | 5/1994 | Campbell et al. ............... 422/3 |
| 5,395,240 A | | 3/1995 | Paschke et al. ............. 433/119 |
| 5,492,671 A | | 2/1996 | Krafft .......................... 422/26 |
| 5,494,637 A | | 2/1996 | Barlow ........................ 422/28 |
| 5,529,750 A | | 6/1996 | Kochte ........................ 422/28 |
| 5,534,221 A | | 7/1996 | Hillebrenner et al. ......... 422/33 |
| 5,558,841 A | * | 9/1996 | Nakagawa et al. ......... 422/105 |
| 5,571,488 A | | 11/1996 | Beerstecher et al. ........ 422/297 |
| 5,759,490 A | * | 6/1998 | Malchesky .................... 422/28 |
| 5,795,403 A | | 8/1998 | Biermaier ................ 134/22.12 |
| 5,833,935 A | * | 11/1998 | Malchesky .................. 422/300 |
| 5,858,305 A | | 1/1999 | Malchesky .................... 422/28 |
| 5,882,589 A | | 3/1999 | Mariotti ....................... 422/28 |
| 5,923,432 A | | 7/1999 | Kral .......................... 356/432 |
| 5,937,875 A | | 8/1999 | Nygren ................... 134/22.11 |
| 6,013,227 A | | 1/2000 | Lin et al. ..................... 422/28 |
| 6,041,794 A | | 3/2000 | Lin et al. ................. 134/22.11 |
| 6,068,815 A | * | 5/2000 | Oberleitner et al. .......... 422/28 |

* cited by examiner

FLUID SPRAY SYSTEM FOR CLEANING AND STERILIZING MEDICAL DEVICES SUPPORTED ON A RACK

BACKGROUND OF THE INVENTION

The present invention relates to the decontamination arts. It finds particular application in connection with an automated system for leak testing, cleaning, sterilizing, and drying devices for medical, dental, mortuary, and pharmaceutical applications, and the like, and will be described with particular reference thereto. It should be appreciated, however, that the invention is also applicable to the decontamination of other devices in an automated processing system.

Medical devices, such as endoscopes, and other lumened instruments, are subjected to thorough cleaning and antimicrobial decontamination between each use. During medical procedures, the devices become coated with blood and other protein-rich body fluids. If the instruments are sterilized while they are coated with these materials, the high temperatures and/or chemicals used in the sterilization process tend to cause the materials to set as a hardened layer of biological residue that becomes difficult to remove. Not only do such residues present a barrier to sterilant penetration, but even when sterilized, they may later break down to form toxic substances which pose hazards to patients when the devices are reused.

Traditionally, such devices are often rinsed in a cleaning solution, such as an enzymatic cleaner, to remove the bulk of the blood and other body fluids from their surfaces. The rinsing process is generally carried out manually, by immersing the devices in a shallow tray of the cleaning solution. However, for devices such as endoscopes, the cleaning fluid may not penetrate the length of the internal lumen, leaving a portion of the endoscope to become coated with dried body fluids. Additionally, the biological materials and strong cleaners may pose hazards to personnel coming into contact with them.

High temperature sterilization processes, such as steam sterilization in an autoclave, are generally unsuited to the sterilization of endoscopes because of the delicate components and materials from which they are manufactured. The high temperature and pressure tend to curtail the useful life of endoscopes, rubber and plastic devices, lenses, and portions of devices made of polymeric materials and the like. High temperature sterilization alone does not clean. Any body fluids that are not removed prior to thermal sterilization are typically baked on to the instrumentation.

Instruments which cannot withstand the pressure or temperature of the oven autoclave are often microbially decontaminated with gas or vapor such as ethylene oxide gas or hydrogen peroxide vapor. Both require a separate cleaning operation. The ethylene oxide sterilization technique also has several drawbacks. First, the ethylene oxide sterilization cycle tends to be longer than the steam autoclave cycle. Second, some medical equipment can not be sterilized with ethylene oxide gas. Third, ethylene oxide is highly toxic and can present health risks to workers if not handled properly.

Biological materials remaining on the instruments after the cleaning process may pose hazards to personnel transferring the instruments to a sterilizer.

Liquid microbial decontamination systems are now utilized for equipment which could not withstand the high temperatures of steam sterilization. Peroxyacetic acid, or peracetic acid, is a useful sterilant and/or disinfectant for a variety of applications, including disinfection of waste and sterilization or disinfection of medical equipment, packaging containers, food processing equipment, and the like. It has a broad spectrum of activity against microorganisms, and is effective even at low temperatures. It poses few disposal problems because it decomposes to compounds which are readily degraded in sewage treatment plants.

In some situations, a technician mixes a disinfectant or sterilant composition with water and then manually immerses the items to be microbially decontaminated in the liquid composition. The high degree of manual labor introduces numerous uncontrolled and unreported variables into the process. There are quality assurance problems with technician errors in the mixing of sterilants, control of immersion times, rinsing of residue, exposure to the ambient atmosphere after the rinsing step, and the like. For sterilizing large instruments, however, a large receiving tray and a considerable quantity of decontaminant solution are used to accommodate and fully immerse the instruments. Manually filling the lumens of elongated instruments, such as endoscopes, was not always reliable.

Integrated decontamination systems, such as peracetic acid decontamination systems, have now been developed which provide a premeasured dose of a decontaminant in solution. Items to be sterilized are loaded into a receiving tray of a sterilization system and a cartridge of concentrated decontaminant inserted into a well. As water flows through the system, the decontaminant, which may be accompanied by surfactants and corrosion inhibitors, is diluted and carried to the receiving tray.

Spraying the exterior of the instruments, while flowing decontaminant solution through the lumens, would have advantages over full immersion of the devices in reducing the quantity of decontaminant solution used. However, because of the complex shape of endoscopes, the spray jets may not reach all of the surfaces of the device.

The present invention provides for a new and improved automated fluid delivery system for reprocessing endoscopes and the like which overcomes the above-referenced problems and others.

SUMMARY OF THE INVENTION

In accordance with one aspect of the present invention, a system for microbially decontaminating a device with at least one internal passage is provided. The system includes a chamber for receiving the device, a source of a microbial decontaminant solution, spray nozzles, disposed within the chamber, for spraying the decontaminant solution over an external surface of the device, and at least one connection port disposed within the chamber for supplying the decontaminant solution to the internal passage. A fluid distribution system fluidly connects the source of the decontaminant solution, the chamber, and the nozzles and connection port. The distribution system delivers the decontaminant solution to the nozzles and connection port and receives sprayed decontaminant solution from the chamber. A pump, fluidly connected with the fluid distribution system, pumps the decontaminant solution to the nozzles and connection port. A control system controls the delivery of the decontaminant solution to the nozzles and connection port.

In accordance with another aspect of the present invention, a method of cleaning and microbially decontaminating a device having at least one internal passage is provided. The method includes positioning the device within a chamber, spraying a washing solution over the device from nozzles within the chamber to remove soil from exterior surfaces of the device and delivering the washing solution to the internal passage of the device to remove soil from the internal passage of the device. The method further includes spraying a microbial decontaminant solution over the device from nozzles within the chamber to microbially decontaminate the exterior surfaces of the device and delivering the microbial decontaminant solution to the internal passage of the device to microbially decontaminate the internal passage of the device.

One advantage of the present invention is that an endoscope or other lumened device is cleaned and microbially decontaminated in a single automated process.

Another advantage of the present invention is that hazards posed to personnel by handling contaminated devices are minimized.

Another advantage of the present invention is that a decontaminant spray system ensures decontamination of all exterior surfaces of the device being decontaminated.

Another advantage of the present invention is that the device being decontaminated is supported in an optimum position for access by the sprayed decontaminant solution.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
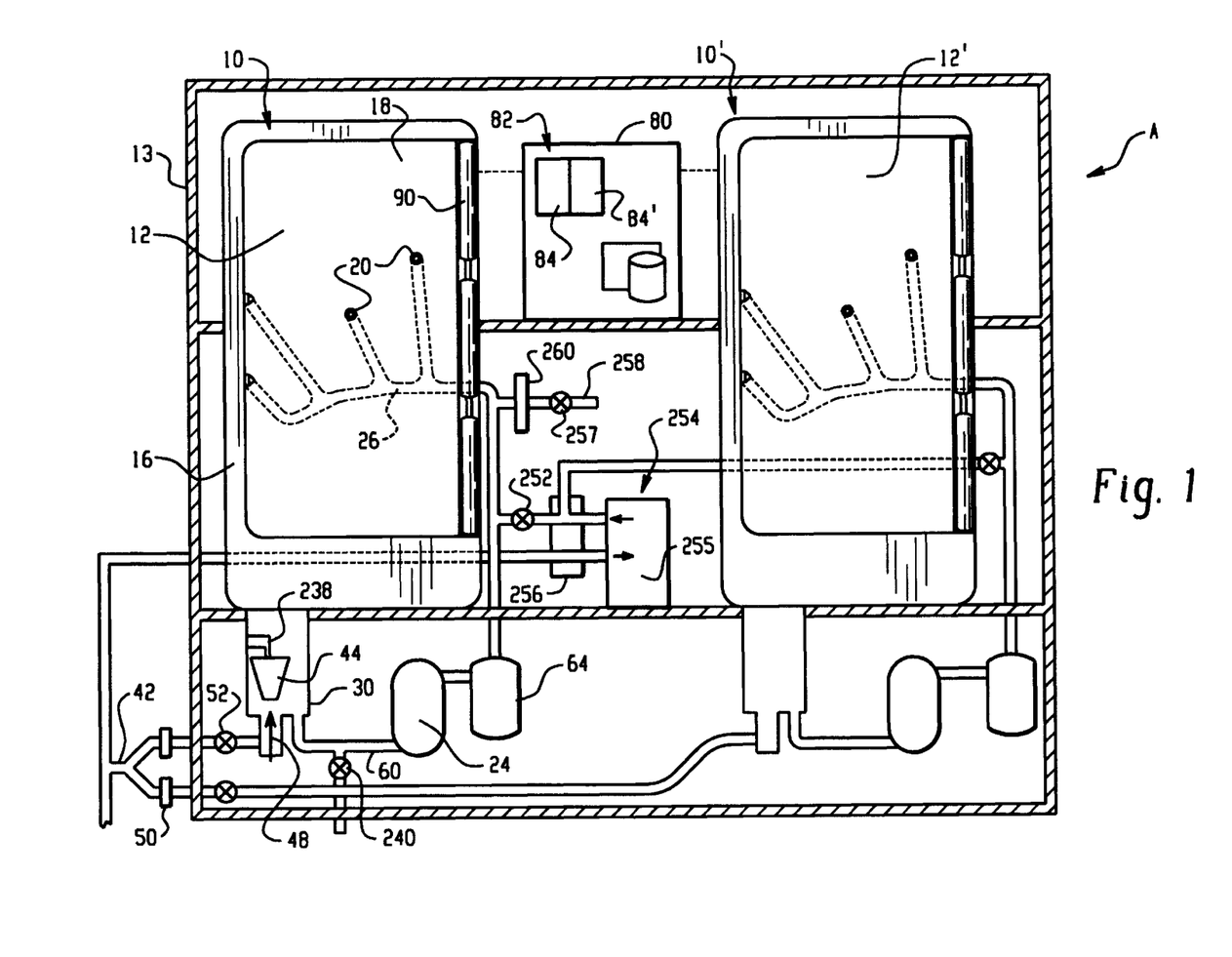
FIG. 1 is a diagram of a cleaning and microbial decontamination system according to the present invention.
Figure 2:
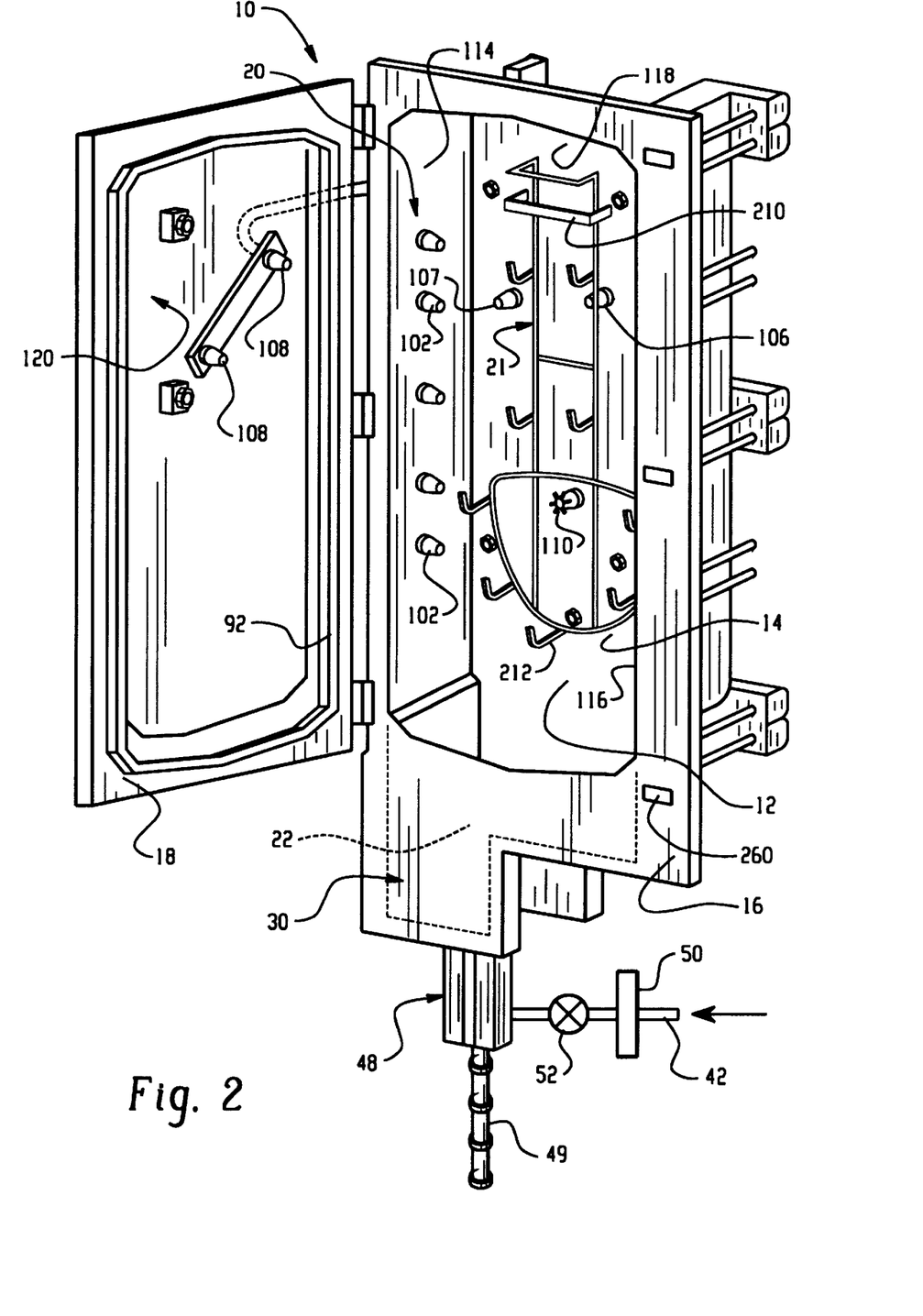
FIG. 2 is a perspective view of the chamber of FIG. 1.

With reference to FIGS. 1 and 2, an automated liquid cleaning and antimicrobial decontamination system A sequentially leak tests and washes then sterilizes or disinfects items, such as medical, dental, and pharmaceutical devices, and the like. While particular reference is made to the cleaning and microbial decontamination of lumened instruments, such as endoscopes, it is to be appreciated that the system A has application in the cleaning and/or decontamination of a variety of different devices. The processor A is particularly suited to the cleaning and microbial decontamination of instruments which are heat labile, i.e., those, which because of their components or materials, may be damaged by temperatures over about 60° C.

The term "endoscope," as used herein, should be understood to include a wide variety of lumened instruments, including angioscopes, artheroscopes, laparoscopes, bronchoscopes, duodenoscopes, catheters, and the like.

The term "microbial decontamination" and other terms relating to decontaminating will be used herein to describe sterilization, disinfection, and other antimicrobial treatments which are designed to destroy microorganisms contaminating the items. The term "washing" will be used herein to describe the physical removal of soil from the items, without necessarily destroying the microorganisms contaminating the items.

The system A includes at least one washing and microbial decontamination cabinet 10 which defines an interior cleaning and microbial decontamination chamber 12. FIG. 1 shows a pair of side-by-side cabinets 10 and 10' which are separately operable. For convenience, only one of the cabinets and its associated hardware will be described. It should be appreciated, however that both cabinets are similarly operated and configured, unless otherwise noted. A housing 13, such as a frame, supports the first and second chambers 12, 12' adjacent each other.

Items to be washed and microbially decontaminated are loaded into the chamber 12 through an opening 14 in a vertical front wall 16 of the cabinet, closed by a door 18. Within the chamber, a fluid distribution system 20, comprising spray jets and connection nozzles, sprays a washing/decontaminant solution over exterior surfaces of the items and directs the solution through internal passages of endoscopes and other objects with lumens. A rack 21 supports one or more endoscopes in a suitable position for optimal effective washing and decontamination by the spray system 20. The endoscope may be loaded on to the rack prior to loading into the chamber, or the rack may be positioned in the chamber prior to attachment of the endoscope.

A collection tank or sump 22 forms the base of the cabinet 10 and receives the sprayed washing/decontaminant solution as it drips off the items. A high pressure pump 24 delivers the washing/decontaminant solution under pressure to the spray system 20 through a fluid distribution system or manifold 26.

A well or mixing chamber 30 sequentially receives doses of a cleaner concentrate and a concentrated decontaminant. The cleaner concentrate mixes with water to form a washing solution for cleaning the items prior to microbial decontamination. The concentrated decontaminant is preferably an antimicrobial agent or comprises reagents which react to form an antimicrobial agent on mixing with water. The cleaner concentrate may be an enzymatic cleaner, or an acid or alkaline cleaner, and may include detergents, surfactants, and the like. A preferred cleaner concentrate is a pH neutral, low foaming composition, which is not harmful to the components of the device. The cleaner concentrate and concentrated decontaminant may be in solid or in liquid form. As shown in FIGS. 1 and 2, the well is integral with the collection tank 22 of the chamber, although a separate well is also contemplated.

A preferred antimicrobial agent is peracetic acid, either in concentrated liquid form, or as a reaction product of powdered reagents, such as acetyl salicylic acid and sodium perborate. A water inlet 42 supplies water, typically from a municipal water system, to the well 30. The water mixes with detergents, surfactants, corrosion inhibitors, pH buffers, the concentrated decontaminant, and other selected components in the well to form wash, decontaminant, or other solutions.

Preferably, the concentrated decontaminant, cleaner concentrate, and the other components (corrosion inhibitors, pH buffers, surfactants, and the like) are supplied in a disposable package or cup 44 which is positioned in the well 30 prior to a decontamination cycle. The cup 44 separately holds the measured doses of the cleaner concentrate, a pretreatment mixture of buffers, surfactants, corrosion inhibitors, and other pretreatment chemicals, and the decontaminant in separate compartments 45, 46, and 47, respectively, for separate release into the system. In this way, the items are first washed and then microbially decontaminated. A cup cutter 48, driven by an air cylinder 49, or other suitable opening member, is positioned at the base of the well 30 for opening selected compartments of the cup as specified times through the course of a reprocessing cycle.

The quantity of water entering the system is regulated to provide a washing/decontaminant solution of a desired concentration in the decontamination chamber 12. The water is preferably passed through a microporous filter 50 in the water inlet line 42 which filters out particulates. A valve 52 in the water inlet 42 closes when the selected quantity of water has been admitted.

Figure 3A:
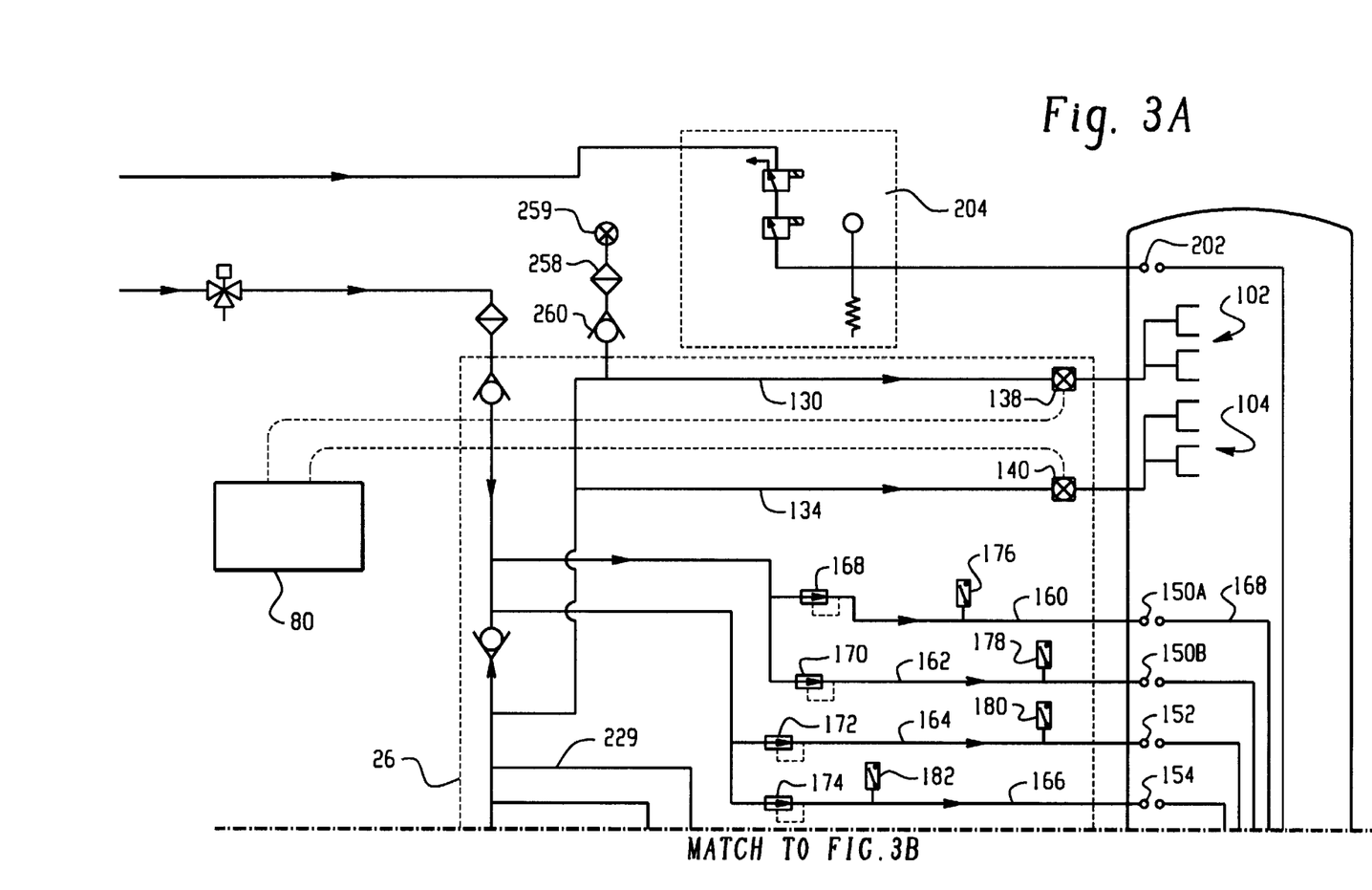
FIG. 3 is a plumbing diagram of the system of FIG. 1, with the door open.
Figure 3B:
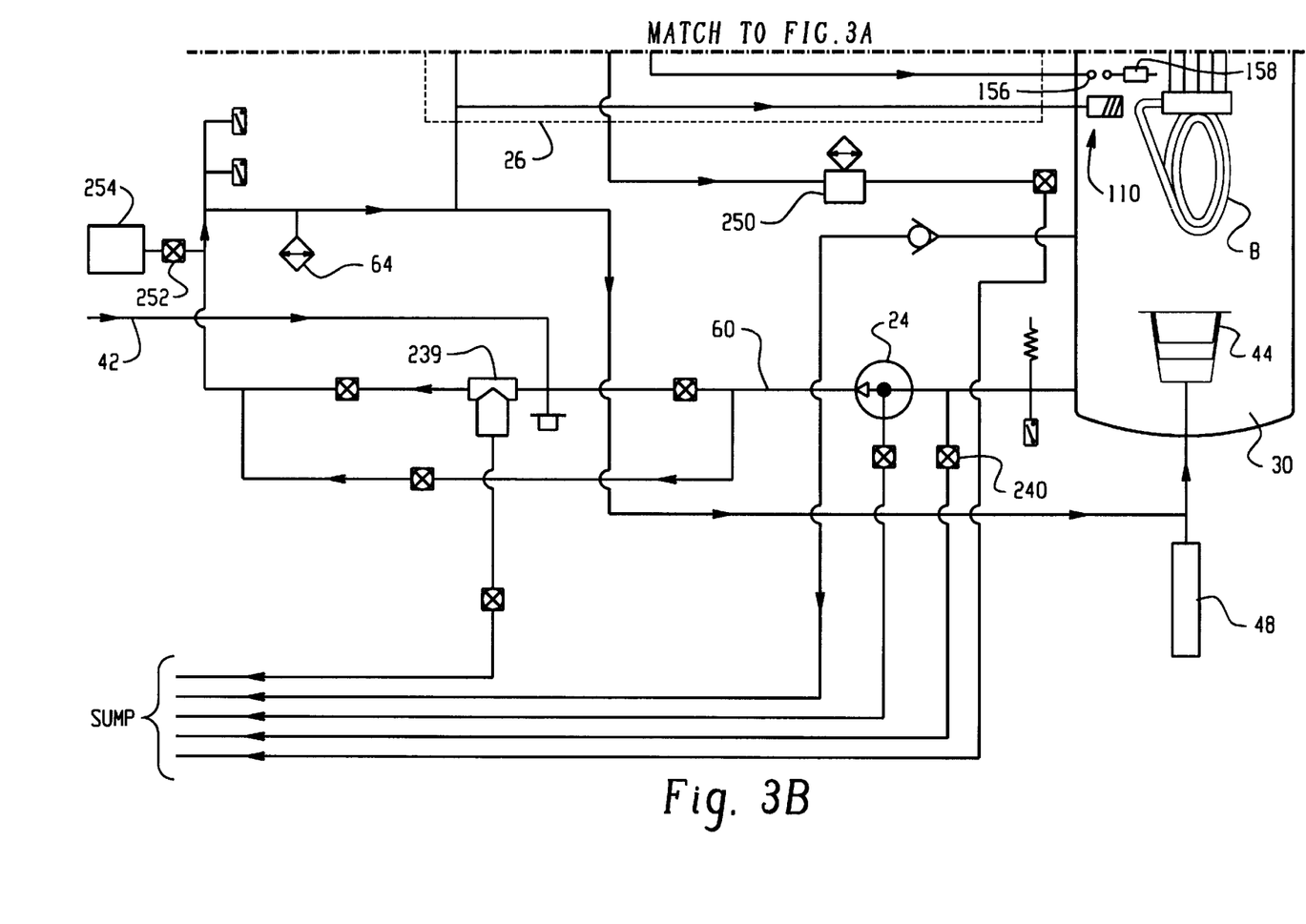

With reference also to FIG. 3, a fluid supply pathway 60 connects the well 30, the pump 24, and the fluid distribution system 26. Thus, a fluid circulation loop is provided, which circulates the washing and decontaminant solutions through the well 30, pathway 60, fluid distribution system 26, and spray system 20. Sprayed solutions collect in the well and are pumped by the pump 22 through the pathway, fluid distribution system, and back to the spray system 20. A heater 64, situated in the fluid supply pathway 60, heats the decontaminant solution and optionally the washing solution and a rinse liquid to a preferred temperature(s) for effective cleaning, decontamination, and rinsing.

A computer control system 80 controls the operation of the system A, including the pump 24, the heater 64, the valves 52, and the like. The control system 80 preferably controls the operation of the second chamber 10' and its analogous pump, heater, valves, and the like. The two chambers, pumps, heaters, etc. are separately and asynchronously controllable so that at any one time either or both chambers may be in operation, and need not be at the same point in a washing and decontamination cycle. The control system 80 includes an operator input panel 82 mounted between the first and second chambers 12, 12'. The input panel includes a first display 84 for indicating the status of a washing/decontamination cycle in the first chamber and a second display 84' for indicating the status of a washing/decontamination cycle in the second chamber.

A door latching mechanism 90 holds the door in the closed position against the front face of the cabinet and prevents the opening of the door during a washing and decontamination cycle. A seal member 92, such as a gasket, is positioned between the door and the front face of the cabinet to provide a fluid tight seal at the pressures used in the cabinet.

Figure 4:
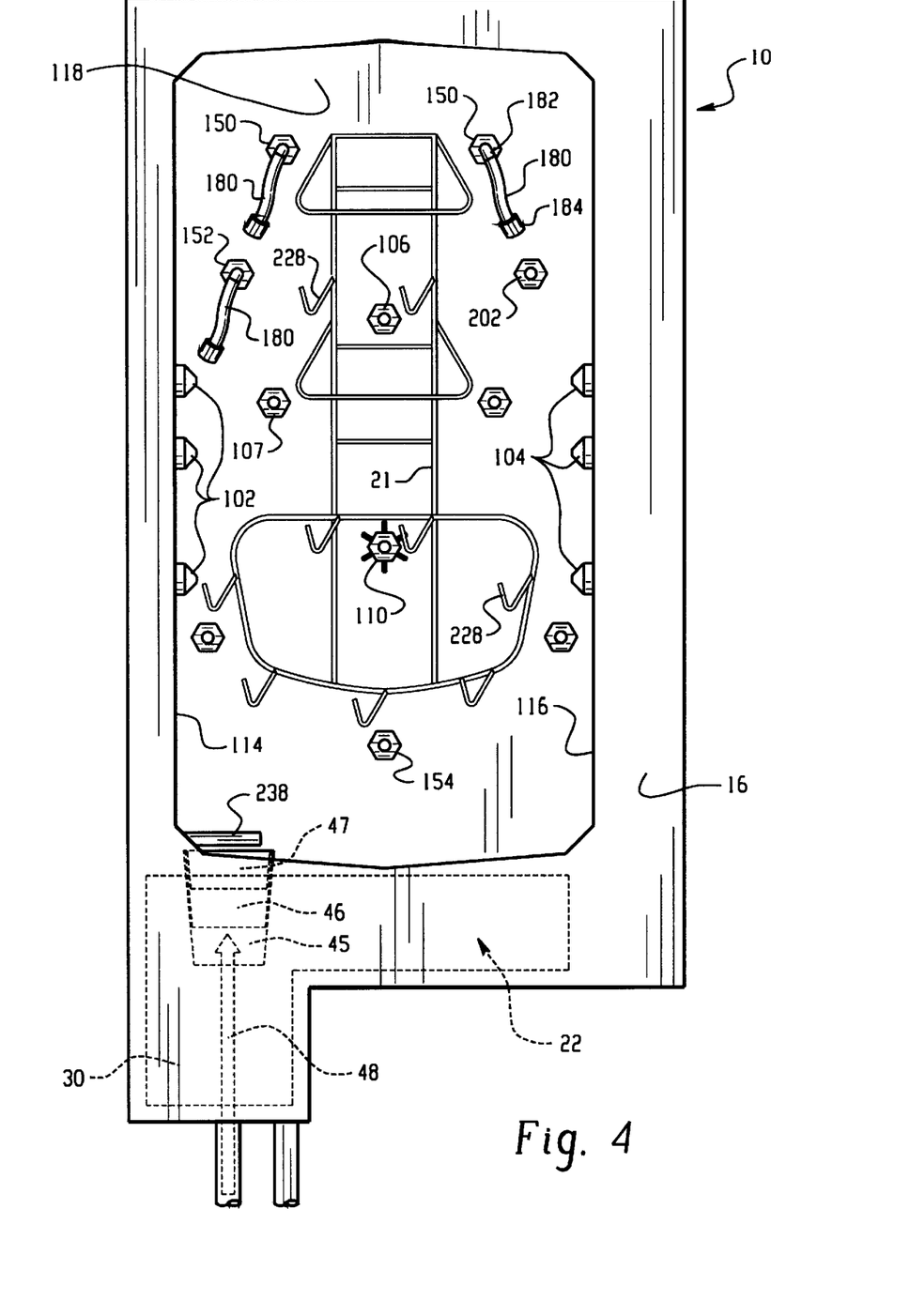
FIG. 4 is a side front view of the chamber of FIG. 2.

With reference to FIGS. 2, 3, and also to FIG. 4, the spray system 20 includes several types of spray nozzles 102, 104, 106, 107, 108, and 110, which direct the cleaning/decontaminant solutions over an endoscope B and other items within the chamber 12 for complete coverage. The pump supplies the nozzles with the washing/decontaminant fluid at a pressure of about 60–80 psi. The spray nozzles 102 and 104 are located on left and right side walls 114, 116 of the chamber 12, respectively. These have a relatively narrow angle of spray, preferably about 90°, for impacting the surfaces of the endoscope at high pressure. Spray nozzles 106 are located on a rear wall 118 of the chamber. These nozzles spray over a wider angle, preferably about 120 degrees, for wider coverage, although with lesser impact than the nozzles 102, 104. The spray nozzle 107 extends forward from the rear wall. It has a narrow spray angle of 45 degrees and is aimed to directly impact a contact point on the device. The spray nozzles 108 are attached to an inner surface 120 of the chamber door 18.

The spray nozzle 110 extends forwardly from the rear wall 118 of the chamber and directs cleaning fluid radially in multiple directions for wide coverage. As shown in FIG. 4, the nozzle 110 includes multiple spray heads. Six spray heads are shown, angled at 60 degrees apart, for a 360 coverage. Alternatively, spray nozzle 110 is a rotating nozzle, which is rotated through a 360 degree path to deliver solution in many directions.

Figure 5:
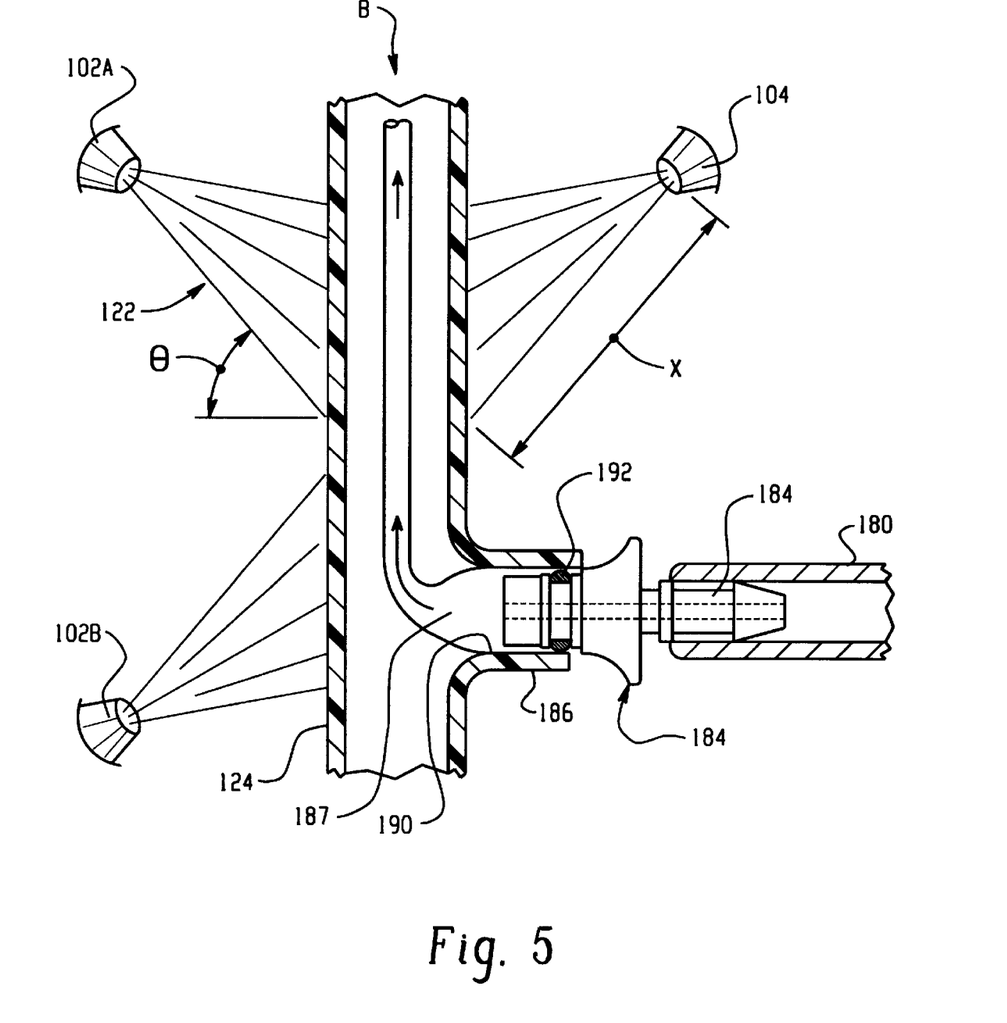
FIG. 5 is a sectional view of a section of an endoscope showing spray jets impinging on its outer surface.

With reference also to FIG. 5, the spray nozzles 102, 104, 106, 108 are angled such that all surfaces of the endoscope B are contacted by the spray of decontaminant solution emitted from the nozzles. Specifically, the rack 21 positions the endoscope such that each nozzle spray jet 122 strikes the endoscope surface 124 at a shallow angle θ, relative to normal to the endoscope surface. Preferably, the angle θ is less than about 45 degrees, i.e., each surface of the endoscope is struck with at least one spray jet at an angle of no more than about 45 degrees from normal. Thus, the nozzles are angled to deliver the decontaminant/cleaning solutions at different angles. For example, as shown in FIG. 5, nozzle 102A is directed downwardly, while nozzle 102B is directed upwardly.

Additionally, each surface of the endoscope is no more than a maximum distance x from the closest spray nozzle, so that the endoscope receives the full force of the spray jet. Preferably, x is no more than 20 centimeters, more preferably, x is less than about 15 centimeters. Further, each surface of the endoscope is no less than a minimum distance from the closest spray nozzle, so that the endoscope receives the full force of the spray jet. Preferably, the minimum distance is at least 5 centimeters.

With reference once more to FIG. 3, to obtain these minimum criteria, the nozzles are in many cases positioned so closely that their sprays may interact. The interaction, prior to contacting the instrument, can negate or alter their force, angle of impact, and other characteristics. To avoid the spray jets 122 from different directions canceling each out, the jets are pulsed in sequence. For example, the manifold 26 includes a first fluid line 130 which supplies nozzles 102 and a second fluid line 134 which supplies nozzles 104. The control system 80 sequentially opens an air diaphragm valve 138 in the first line 130 for a few seconds, allowing the cleaning/decontaminant solution to flow to nozzles 102, then opens an air diaphragm valve 140 in the second line 134 for a few seconds, allowing the cleaning/decontaminant solution to flow to nozzles 104.

With reference now to FIGS. 2 and 3, the spray system 20, in addition to the nozzles, also includes several connection ports 150, 152, and 154, for supplying washing/decontaminant and rinse solution to the internal passages of the endoscope B and an associated set of biopsy forceps. An additional port 156 may be provided for supplying the solutions to a valve reprocessor 158. The different internal passages of a typical endoscope and biopsy forceps are rated to withstand different maximum pressure. The connection ports supply washing/decontaminant solution at an appropriate pressure that is below the maximum pressure rating for the passage to which the connection port supplies solution. For example, as shown in FIG. 3, the manifold includes fluid lines 160, 162, which supply fluids to connection ports 150A and 150B at a first pressure, preferably of no more than about 20 psi, for washing/decontaminating the lumens, and line 164, which supplies connection port 152 at a second pressure, preferably of no more than about 240 mmHg (40 psi), for washing/decontaminating the elevated guide wire passages. Another fluid line 166 supplies connection port 154 at a third pressure, preferably of no more than about 240 mmHg (40 psi), for cleaning/decontaminating the biopsy forceps. Pressure regulators 168, 170, 172, and 174 in each of the fluid lines 160, 162, 164, and 166 are set to ensure that the maximum pressure is not exceeded. Pressure switches 176, 178, 180, 182 detect the presence of a pressure drop in the lines 160, 162, 164, and 166 is met.

With reference once more to FIGS. 4 and 5, the connection ports 150, 152, and 154 are connected with the respective internal passages of the endoscope and biopsy forceps by tubes 180, each with a quick connect 182 at the connection port end and a suitable connector 184 at the other end for connecting with the inlet port 186 of the respective internal passage, for releasably and quickly connecting the fluid lines with the respective internal passages 187. To avoid confusion and accidental over-pressurization of the lumens, the quick connects 182 for the low pressure lines 160, 162, 166 will not connect with the high pressure connection port 152. In the preferred embodiment, the connectors have different sizing; but, different shapes and the like are also contemplated.

The connectors 184 are preferably leaking connectors, i.e., they allow a controlled portion of the washing/decontaminant solution to flow between the connector and the inlet port to contact all adjacent surfaces 190 of the inlet port 186. This ensures that all the accessible surfaces of the internal passage 187 are contacted with the washing/decontaminant solution. The portion of the washing/decontaminant solution which leaks from around the connector is only a small portion of the solution entering the inlet port. The relative flow is balanced for an optimum cleaning of all points.

In the embodiment of FIG. 5, the leaking connector 184 includes a metal C ring 192, which is seated loosely in an annular groove in a portion of the connector which is received past a small internal lip of the inlet port 186. The ring spaces the connector from the internal surfaces 190 of the inlet port, allowing a portion of the fluid to flow around it and out of the inlet port 186. Other configurations of male and female leaking connectors are also contemplated. Analogous leaking plug members are used to imperfectly block selected ports.

With reference to FIG. 3, a further connection port 202 in the chamber connects a leak detector 204 with the venting connector port of the endoscope for testing the endoscope for leaks. If leaks are found, the leak detector aborts the cycle to prevent fluids from leaking into sensitive regions of the endoscope. Repairs are made to the endoscope, if appropriate, prior to subjecting the endoscope to further leak testing and cleaning.

Figures 6, 6A:
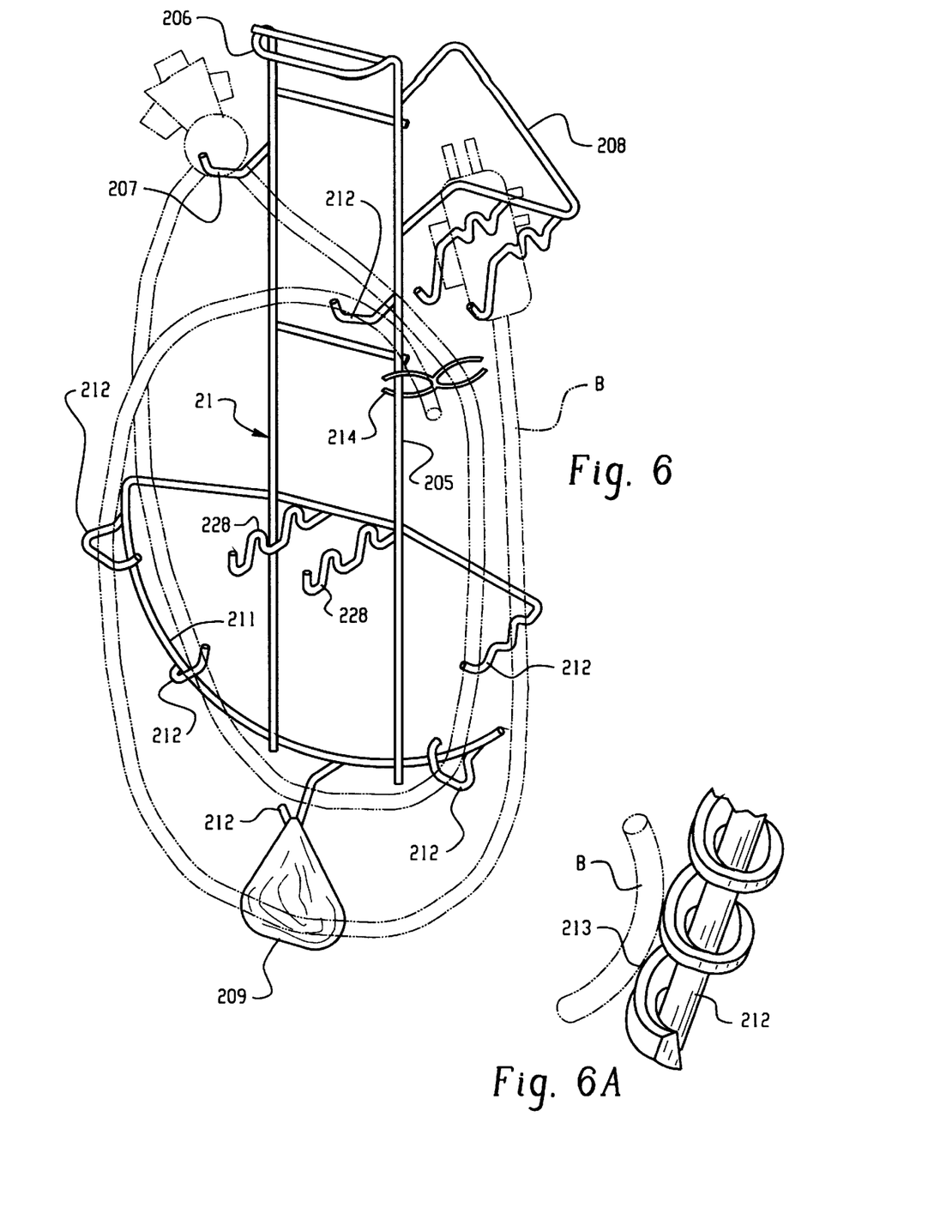
FIG. 6 is a perspective view of the endoscope rack of FIGS. 2 and 4 with an endoscope shown in phantom.
FIG. 6A is an enlarged perspective view in partial section of a rack peg of FIG. 6.

With reference once more to FIG. 2 and reference also to FIG. 6, the rack 21 is preferably removable from the chamber 12. To accommodate different types of endoscopes, several racks 21 are provided, each one configured for receiving a particular type or family of endoscopes. The appropriate rack is selected according to the endoscope to be reprocessed, and the endoscope fitted to the rack prior to or after hooking or otherwise attaching the rack within the chamber. The rack includes a central rectangular support frame 205 with a carrying and connecting handle 206 attached at an upper end thereof. Mounted on the frame are support members 207, 208, which are configured for receiving the endoscope operating section and light guide connector sections, respectively. Small, separate components of the endoscope, such as hoods, plugs, and other semi-reusable items, may be hung from the rack in a porous bag 209. The upper end of the rack is releasably mounted on a suitably receiving member or members 210 within the chamber.

The rack includes an arcuate portion 211 which supports a number of pegs or tabs 212. The pegs on the arcuate section and the support frame 205 define a circle for support of the flexible tubes (the umbilical cable and the insertion tube) of endoscope B such that the tubes curve in a wide loop on the rack 21. Preferably, the rack and hooks position the endoscope such that it is not bent sharper than its minimum bend radius. In the preferred embodiment, the bend radius is at least 18 centimeters, i.e., no portion of the flexible portions of the endoscope tubes are bent into a curve which has a radius of less than about 18 cm. This ensures that, as the endoscope is wrapped around the pegs 212, it is correctly positioned for receiving the full force of the spray jets and that there are no inaccessible or potentially damaging tight bends in the endoscope. Depending on the stiffness of the flexible tube, the tube is mounted inside and/or over the pegs. The pegs are positioned at angular intervals such that the end of the tube of every endoscope in the family ends up near, but just beyond, one of the pegs.

The rack is preferably formed from stainless steel, or formed from other materials, which are resistant to the decontaminant solution and other chemicals employed in the chamber.

To minimize contact with the endoscope, and improve access of the spray of washing or decontaminant solutions to the contact areas, the support members 207, 208, and pegs 212, preferably make only "point contact" with the endoscope, i.e., the area of contact is as small as is possible, without resulting in damage to the endoscope. In one preferred embodiment, the pegs and support members are formed from a screw-threaded stock, which contacts the endoscope only at tips 213 of the threads, as shown in FIG. 6A. Preferably, the tips of the threads are blunted, such as acme threads or threads with a sinusoidal or other curved cross section, to avoid indentation, scratching, or other damage to the endoscope.

Figure 7:
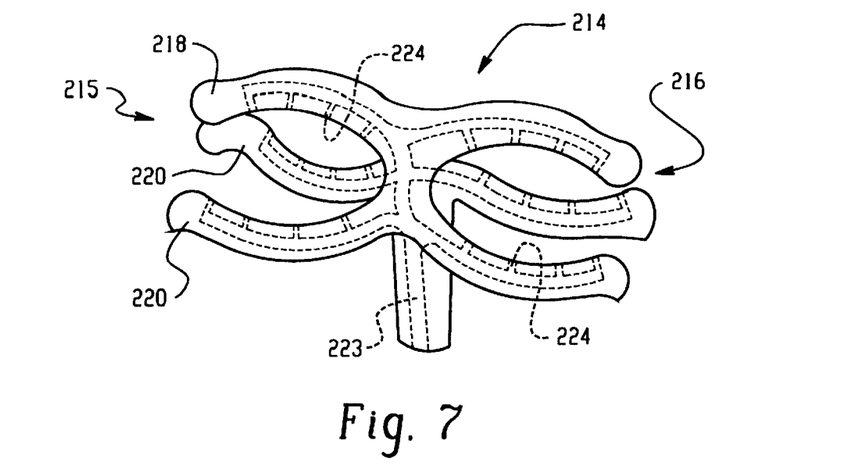
FIG. 7 is a perspective view of one embodiment of an endoscope clip.
Figure 8:
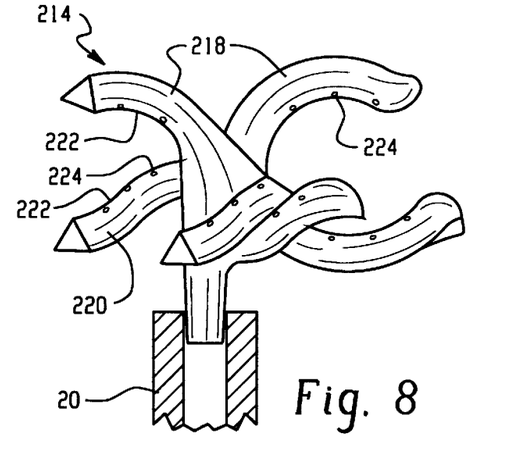
FIG. 8 is a perspective view of the endoscope clip of FIG. 7 showing the fingers in partial section.
Figure 9:
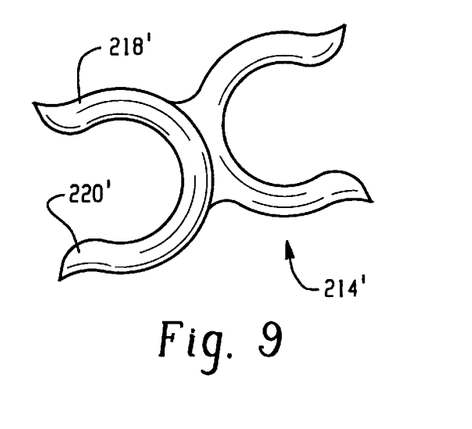
FIG. 9 is a perspective view of another embodiment of an endoscope clip.

With reference also to FIGS. 7 and 8, one or more clips 214 is attached to the tip of the endoscope insertion tube, or other flexible, tubular portion of the endoscope, to prevent it swaying and breaking during transport or during the cycle. The clip includes a first gripping portion 215, which releasably grips the tip of a flexible portion of the endoscope B and a second gripping portion 216, which releasably grips another portion of the endoscope or the rack 19. Each of the gripping portions includes at least one upper finger 218 and at least one lower finger 220. The clip 214 of FIGS. 7 and 8 includes one upper finger and two, spaced lower fingers. FIG. 9 shows an alternative embodiment of a clip 214', where each gripping portion includes one upper finger 218' and one lower finger 220'. Other embodiments of the clip are also contemplated. For example, the clip could be permanently attached to the rack 21 and have only a single gripping portion for gripping the endoscope tip.

The clip 214, 214' is preferably formed from a resiliently flexible material, such as Nylon or Delrin®. Accordingly, when the tubular portion to be gripped (e.g., the endoscope tip or rack) is pressed against the tips of the fingers 218, 220, the upper and lower fingers are splayed apart, allowing the tubular portion to be inserted therebetween. The fingers 218, 220 then snap back to grip the tubular portion firmly, but not so tightly that access of the washing and decontaminant solutions is prevented. The material selected for forming the clip is also one which is resistant to the chemicals used in the washing and microbial decontamination system.

With particular reference to FIG. 8, it is important to minimize the contact area between the clip 214, 214' and the endoscope tip to ensure complete sterilization of the outer surfaces of the endoscope. To achieve this, the fingers 218 and 220 have a triangular cross section with a ridge 222 of the triangle, of very small radius, in contact with the endoscope (essentially point contact). This reduces shadowing, i.e., the interference of the clip with the spray jets. Additionally, providing two, spaced apart lower fingers 220 allows the solutions to contact the endoscope tip between the fingers while maintaining a firm grip on the tip. To avoid damage to the endoscope, the contacting ridge 222 is slightly rounded rather than defining a sharp point. The shape of the ridge is optimized to minimize contact while avoiding damage or indentations in the tip.

Optionally, the clip 214 is fluidly connected with the fluid distribution system 20. A fluid pathway 223 inside the clip selectively connects the fluid distribution system with apertures 224 defined in the ridges 222. The washing and decontamination fluids flow out of the apertures 224 and over the surfaces of the endoscope in contact with the clip which otherwise may escape the full force of the spray jets from the nozzles.

Preferably, several interchangeable clips 214 of different dimensions are provided so that an appropriate clip may be selected according to the dimensions of the endoscope/tip.

Optionally, the rack 21 includes support members 228, for supporting coiled biopsy forceps, which are designed to pass through a channel of the endoscope, or other accessories to be cleaned and decontaminated. To anchor the forceps more securely, they are preferably coiled on a carrier which is supported on pegs 228.

The rack 21 and clip(s) 214 are designed to hold the endoscope firmly to avoid damage, but yet allow a small amount of movement (i.e., wobbling) of the endoscope during processing, facilitated by the pulsing of the spray jets. This movement allows access of the solutions to those areas of the endoscope making contact with the rack pegs, support members and clips to ensure that the entire exterior surface of the endoscope is thoroughly cleaned and microbially decontaminated.

Figure 10:
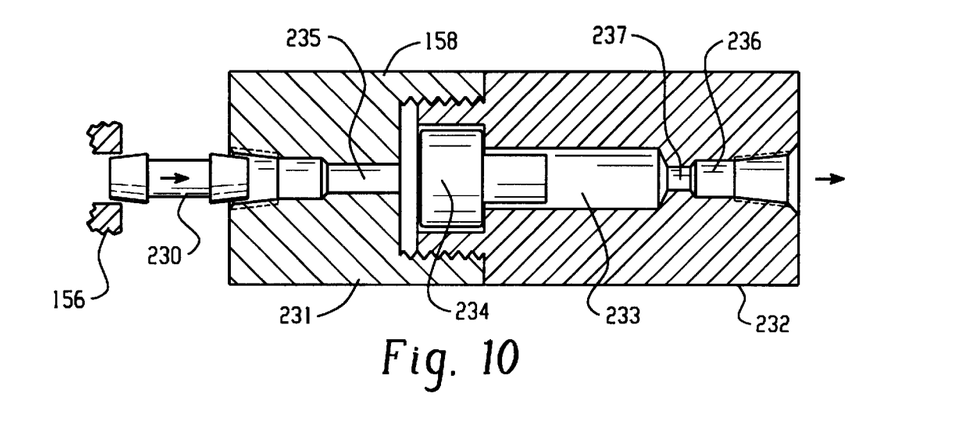
FIG. 10 is an enlarged side sectional view of the valve reprocessor of FIG. 3.

With reference now to FIGS. 3 and 10, a fluid supply line 229 connects the fluid distribution system with the connection port. The valve reprocessor 158 is releasably connected to connection port 156 within the chamber by a quick connect 230, or other suitable connection member. The valve reprocessor includes cap and base portions 231 and 232 which are threadably connected to define an interior chamber 233, which receives an endoscope valve 234, and inlet and outlet passages 235, 236. The cap 231 is sized such that, when the cap is threadably connected to the base 232, the valve head is compressed to its open position. This allows the washing and decontaminant solutions to flow over and through the valve. A restriction 237 in the outlet passage maintains the solutions under pressure as they pass through the valve.

In a typical washing and decontamination cycle, the endoscope B to be cleaned is mounted on the rack 21 and inserted into the chamber 12 with other items to be cleaned and decontaminated. The tubes 180 are connected with their respective endoscope inlet ports 186 and connection ports to connect the endoscope internal passages with the fluid lines. The biopsy forceps are loaded on the rack 21. The leak detector 204 is connected with the endoscope venting connector port. A fresh cup 44 of concentrated decontaminant and other components is inserted into the well 30 and a restraining member or lid 238 positioned over the cup.

Once all the items are properly positioned and fluid lines connected, the door is closed. The entire process, including leak testing, washing, microbial decontamination, and rinsing steps, is fully automated. There is no need for an operator to contact the items until all of the steps are complete.

The control system 80 signals the leak tester 204 to check the endoscope for leaks. If all is satisfactory, the items may be subjected to a prerinse operation, in which the items are sprayed and flushed internally with warm (about 30–35° C.) water for about one minute to remove the bulk of surface contamination. The computer control. 80 signals the valve 52 in the water inlet line 42 to open, allowing water to circulate through the well and the fluid lines 60. The temperature of the water is selected to prevent protein denaturation. Denatured proteins adhere to surfaces and are difficult to remove. Accordingly, the water is kept below 40° C. to prevent this denaturation.

All of the soil and other debris which is rinsed of the device is captured in a filter 239, such as a backwashable drain strainer, and is not recirculated through the fluid distribution system. At the end of the washing and decontamination cycle, the filter 239 is flushed to remove any debris. After about 1 minute of prerinsing, the control system signals a drain valve 240 in the fluid line 60 to open and the rinse water is flushed from the system A to the drain.

The computer control 80 then signals the valve 52 in the water inlet line 42 to open again, allowing water to circulate through the well and the fluid lines 60. The computer signals the opening member 48 to open the cleaner compartment 45 of the cup. The computer control 80 signals the valve 52 in the water inlet line 42 to open, allowing water to circulate through the well and the fluid lines 60. The cleaner concentrate mixes with the water to form the washing solution and is delivered by the pump 22 under pressure to the nozzles 102, 104, 106, 108, 110 and endoscope connection ports 150, 152, 154, 156. The nozzles spray the washing solution over the outer surfaces of the items while the connection ports deliver the solution to the internal passages, thereby cleaning inner and outer surfaces simultaneously. Sprayed washing solution, which drips off the items, is collected in the sump 22. The pump 22 returns the collected solution from the sump to the fluid supply line 60, preferably after first passing at least a part of the collected solution through the well 30 to ensure complete mixing of the concentrated cleaner in the solution.

The washing solution removes most of the remaining soil from the items, leaving them relatively clean, but not necessarily free of viable microorganisms. Once the washing solution has been circulated through the system for sufficient time to remove all or substantially all of the soil from the endoscope and other items, the control system signals the drain valve 240 in the fluid line 60 to open and 20 the washing solution is flushed from the system A to the drain. Optionally, the water inlet valve 52 is opened to allow additional fresh water into the system to flush the cleaning fluid from the fluid lines 60,24 and the well 30. The drain valve 240 is then closed.

The control system opens the valve 52 for a period to allow more water into the system and signals the cup cutter 48 to open the second compartment 46 of the cup, containing the pretreatment components. These are released into the fluid lines and are circulated through the system as a pretreatment solution. Once sufficient water has entered the system for carrying out the decontaminant part of the cycle, the control system 80 signals the valve 52 to close. The pump 22 circulates the pretreatment solution so that the pretreatment chemicals are distributed throughout the system A and over the items to be microbially decontaminated, prior to admission of the decontaminant. The buffers present buffer the water in the fluid lines to an appropriate pH (typically pH 5–9) for effective decontamination. The corrosion inhibitors present coat the system and the surfaces of items to be decontaminated with traces of inhibitors to provide resistance to the corrosive effects of the decontaminant. Surfactants present improve penetration of the decontaminant into less accessible areas of the device.

Although the pretreatment components may be alternatively included in one or other of the cleaner and decontaminant compartments 45, 47 their effectiveness is lessened. By releasing inhibitors at the same time as the microbial decontaminant, the decontaminant has the opportunity to corrode metal parts before the inhibitors have developed protective barriers around the parts. The buffers modify the pH of the fluid circulating in the system to a neutral pH of about 6–8. Until the buffer has circulated throughout the system, the microbial decontaminant is not fully effective. Additionally, such agents may degrade the microbial decontaminant during storage. Accordingly, it is preferable to provide a separate compartment 46 for the pretreatment components and allow them to circulate through the system for a period of time before introducing the decontaminant.

After a preselected period of circulation, the control system 80 signals the cutter assembly to open the third compartment 47. The decontaminant then mixes with the pretreatment components in the fluid lines 60, 24 and is sprayed through the nozzles 102, 104, 106, 108, 110 and delivered to the endoscope connection ports 150, 152, 154, 156, so that the decontaminant solution flows over the exterior surfaces and through the internal passages of the items to be decontaminated. The nozzles pulse the decontaminant fluid in a preselected sequence to ensure full coverage of the spray. A sensor 250 in fluid communication with one of the fluid flow lines 60, 24 optionally detects the concentration of the decontaminant in the circulating fluid to ensure that a threshold concentration for effective decontamination is provided.

The chamber is maintained under a slight positive pressure during decontamination to minimize ingress of outside air into the chamber.

After a period of circulation of the decontaminant solution sufficient to effect decontamination of the items, the drain valve 240 in the system A is opened and the decontaminant solution flushed from the system A to the drain.

The drain valve 240 is kept open and the control system opens a valve 252 to allow a source 254 of sterile rinse water to supply sterile water to the fluid lines 60 for rinsing the decontaminated items without risk of recontamination of the decontaminated items. The source of sterile water preferably comprises a water heater 255 which heats incoming tap water to a sufficient temperature (preferably about 150° C.) to destroy microorganisms in the water, and a heat exchanger 256, which transfers excess heat from the sterilized water to the incoming tap water. The water heater provides water virtually on demand, eliminating the need to store large quantities of sterile water. Alternatively, the water inlet valve 52 is opened once more to provide rinse water for rinsing the decontaminated items.

The system A has a fill of about 9 liters. A typical cycle includes 6 fills, for a total fluid requirement of 54 liters, as follows:

1) for pre-rinsing,
2) for forming the washing solution,
3) rinsing the washing solution from the system,
4) for forming the pretreatment and decontaminant solution, and
5) and 6) for sterile rinsing.

The control system signals a valve 257 in an air line 258 to open supply microbe-free air to the system to dry the decontaminated items. The air is preferably passed through a microbial filter 260 before entering the system. The air line is connected with the manifold 26 so that the air flows through the nozzles and connection ports, drying the interior and exterior surfaces of the endoscopes and other items. The regulator valves 168, 170, 172, and 174 ensure that the internal passages of the endoscope B are not pressurized beyond their recommended pressure ratings.

At the end of the cycle, the control system 80 signals the cutter assembly 48 to retract from the cup 44 to its starting position.

Because the steps of leak testing, washing, decontaminating, rinsing, and air drying are carried out automatically and sequentially within the chamber, the entire reprocessing cycle can be carried out in a relatively short period of time, typically 30 to 40 minutes for full sterilization, less for high level decontamination. The endoscopes are thus ready for reuse in a much shorter time than conventional cleaning and decontamination processes, in which an operator carries out reprocessing steps using a number of separate pieces of equipment.

The dried items are removed from the decontamination chamber 12 for immediate use or transferred to sterile pouches and stored until needed. The rack 21 can be used to transport the endoscope B to a storage cabinet or to a surgery. The rack handle is configured for carrying the rack and for supporting the rack in the storage cabinet. Thus, the endoscope need not be touched until it is to be used in a surgical procedure, minimizing potential contamination.

Optionally, the device B is enclosed in a sterile pouch before removal from the chamber, to minimize airborne re-contamination prior to reuse. For example, the device may be wrapped in a bag, within the chamber, prior to opening of the door. This may be achieved by suitable controls, or manually, for example with a glove box-type of device in which the operator removes the various connectors from the device and wraps the device in the bag using sterile gloves (not shown) which extend into the chamber.

In an alternative embodiment, the chamber 12 acts as a sterile pouch and is hermetically sealed and disconnected from the rest of the processor A and transported to the site at which the decontaminated items are to be used.

Suitable concentrated cleaning agents are low foaming detergents or enzymatic cleaners, with a pH close to neutral (preferably pH 6–8), to minimize corrosion of metal components.

Various antimicrobial agents may be utilized for the decontaminant. In a preferred embodiment, the decontaminant is a solution of peracetic acid. However, it is also contemplated using other liquid or powdered decontaminants or reagents which react in a common solvent to generate peracetic acid, chlorine, hydrogen peroxide, hypochlorous acid, hypochlorite, or other strong oxidants which have biocidal effects. Aldehydes, such as glutaraldehyde, may be used, but the decontaminant solution should be collected after use and properly treated, rather than disposed of via the drain.

Preferably, the pretreatment agent includes a buffer and a corrosion inhibitor. One preferred buffering system includes a combination of monosodium phosphate, disodium phosphate and hexametaphosphates. Such a buffering system also provides anticorrosion properties. Wetting agents and other corrosion inhibitors may alternatively be used. Preferred copper and brass corrosion inhibitors include azoles, benzoates, other five-membered ring compounds, benzotriazoles, polytriazoles, mercaptobenzothiazole, and the like. Other anti-corrosive compounds include phosphates, molybdates, chromates, dichromates, tungstates, vanadates, borates, and combinations thereof.

The corrosion inhibitory agents are selected in accordance with the nature of the materials in the items being cleaned and/or decontaminated with the decontaminant. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and ortho-phenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$).

Copper and brass corrosion inhibitors include triazoles, azoles, benzoates, polyltriazoles, dimercaptothiadiazoles, and other five-membered ring compounds. Particularly preferred copper and brass corrosion inhibitors include sodium salts of benzotriazole and polyltriazole which are preferred due to their stability in the presence of strong oxidizing compounds. Mercaptobenzothiazole can also be utilized but is apt to be oxidized or destabilized by strong oxidizers. Salicylic acid is an example of an acceptable benzoate corrosion inhibitor.

In hard water, phosphate buffers and corrosion inhibitors tend to cause calcium and magnesium salts present in the hard water to precipitate and coat the instruments being decontaminated and/or cleaned and also leaves deposits on parts of the system. In such cases, a sequestering agent appropriate to prevent precipitation such as sodium hexametaphosphate (HMP), or trisodium nitrolotriacetic acid (NTA $Na_3$) is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated. However, to ensure universal applicability with any water that might be utilized, the presence of a sequestering agent is preferred.

Surface energy reducing agents (surfactants/wetting agents) are preferably agents to increase penetration into crevices of items being treated. This is particularly important when cleaning and decontaminating complex medical instruments which may contain microbial contaminants in crevices, joints, and lumens. Surface energy reducing agents usable in accordance with the present invention include anionic, cationic, nonionic, amphoteric, and/or zwitterionic surfactants. Specific classes of surfactants which are useful include anionic and nonionic surfactants or combinations thereof. Examples of nonionic surfactants usable in the present invention include surfactants such as fatty alcohol polyglycol ethers, nonylphenoxypoly (ethyleneoxy) ethanol, and ethoxylated polyoxypropylene. Specific examples include Genapol UD-50™, Igepal™, Fluowet™, and Pegal™. The surfactants set forth above may be used alone or in combination with each other.

Amounts of the corrosion inhibitors and surfactants to be used in the peracetic acid solution will vary depending upon the type of agent being added and whether or not one or more agents are added.

The inorganic corrosion inhibitors are preferably present in amounts ranging from about 0.01% to 20.0% weight per volume (w/v). Organic corrosion inhibitors are preferably present in amounts ranging from about 0.01% to 0.5% w/v. Phosphates are effective at concentrations in the range of about 0.01% to about 11.0% w/v.

The surfactants are preferably present in amounts ranging from about 0.0001% to about 5.0% w/v. More preferably, the surfactant is present in amounts ranging from about 0.0001% to about 0.5% w/v.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for cleaning and microbially decontaminating a device with at least one internal passage, the system including:
   a chamber for receiving the device in a vertical orientation;
   a source of a microbial decontaminant solution;
   spray nozzles, disposed within the chamber, for spraying the decontaminant solution over an external surface of the device;
   at least one connection port disposed within the chamber for supplying the decontaminant solution to the internal passage;
   a fluid distribution system connecting the source of the decontaminant solution, the chamber, and the nozzles and connection port, the distribution system delivering the decontaminant solution to the nozzles and connection port and receiving sprayed decontaminant solution from the chamber;
   a pump, connected with-the fluid distribution system which pumps the decontaminant solution to the nozzles and connection port; and
   a removable rack, removably hanging within the chamber, for suspending the device in the vertical orientation, such that decontaminant solution sprayed from the nozzles drips from the device, the rack having a plurality of pegs which define a curve.

2. A system for cleaning and microbially decontaminating an endoscope, the system comprising:
   a chamber for receiving the endoscope;
   a source of a microbial decontaminant solution;

spray nozzles, disposed within the chamber, for spraying the decontaminant solution over an external surface of the endoscope;

at least one connection port disposed within the chamber for supplying the decontaminant solution to an internal passage of the endoscope;

a fluid distribution system connecting the source of the decontaminant solution, the chamber, and the nozzles and connection port, the distribution system delivering the decontaminant solution to the nozzles and connection port and receiving sprayed decontaminant solution from the chamber;

a pump, connected with the fluid distribution system which pumps the decontaminant solution to the nozzles and connection port;

a removable rack, supported within the chamber, for positioning the endoscope within the chamber;

an endoscope clip which releasably couples a tip portion of the endoscope to one of the rack and another portion of the endoscope, to keep the tip portion securely positioned, the clip being adapted for interconnection with the fluid distribution system and including:
 at least one upper finger and at least one lower finger, apertures defined in the fingers for delivering decontaminant solution to portions of the endoscope contacted by the fingers, and
 a fluid pathway inside the clip which connects the fluid distribution system with the apertures; and a control system which controls the delivery of the decontaminant solution to the nozzles and connection port.

3. A system for cleaning and microbially decontaminating a device, the system comprising:

a chamber for receiving the device;

a source of a microbial decontaminant solution;

spray nozzles, disposed within the chamber, for spraying the decontaminant solution over an external surface of the device;

a pump which pumps the decontaminant solution to the nozzles; and a control system which controls the delivery of the decontaminant solution to the nozzles, the control system sequentially causing a first set of the spray nozzles to spray the decontaminant solution for a first period of time and then causing a second set of the spray nozzles to spray the decontaminant solution for a second period of time.

4. The system of claim 3, further including a nozzle assembly disposed adjacent a geometric center of the chamber that sprays radially outward.

5. The system of claim 4, wherein the nozzle assembly includes at least one of:
 a plurality of stationary nozzles mounted on a central support and directed radially outward; and
 a rotating nozzle.

6. The system of claim 3, wherein the nozzles of the first and second sets are aimed such that their spray patterns cross.

7. A system for cleaning and microbially decontaminating a device with at least two internal passages, the system comprising:

a chamber for receiving the device;

a source of a microbial decontaminant solution;

spray nozzles, disposed within the chamber, for spraying the decontaminant solution over an external surface of the device;

at least two connection ports disposed within the chamber for interconnection with the at least two internal passages for supplying the decontaminant solution to the at least two internal passages;

a fluid distribution system connecting the source of the decontaminant solution, the chamber, and the nozzles and connection ports, the distribution system delivering the decontaminant solution to the nozzles and connection ports and receiving sprayed decontaminant solution from the chamber, the fluid distribution system including:
 a first fluid pathway connected with a first connection port;
 a first regulator regulating the pressure of the decontaminant solution flowing through the first fluid pathway to a first internal passage of the device;
 a second fluid pathway connected with at least a second connection port; and
 a second regulator regulating the pressure of the decontaminant solution flowing through the second fluid pathway to a second internal passage of the device, such that maximum pressure ratings of the first and second internal passages are not exceeded;

a pump, connected with the fluid distribution system which pumps the decontaminant solution to the nozzles and connection ports; and a control system which controls the delivery of the decontaminant solution to the nozzles and connection ports.

8. The system of claim 7, further including:
a housing which supports the first chamber and the second chamber adjacent each other with an operator input panel mounted adjacent the first and second chambers.

9. The system of claim 7, wherein the input panel includes a first display for indicating a status of a washing/decontamination cycle in the first chamber and a second display for indicating a status of a washing/decontamination cycle in the second chamber.

10. The system of claim 7, further including:
a sterile water generator connected with the fluid distribution system which sterilizes unsterile water and supplies the sterile water to the nozzles and connection ports for rinsing the device.

11. The system of claim 7, further including:
an air inlet connected with the fluid distribution system, for supplying filtered air to the spray nozzles and connection ports to dry the device.

12. A system for cleaning and microbially decontaminating an endoscope, the system comprising:

a chamber for receiving the endoscope;

a source of a microbial decontaminant solution;

spray nozzles, disposed within the chamber, for spraying the decontaminant solution over an external surface of the endoscope;

a fluid distribution system connecting the source of the decontaminant solution, the chamber, and the nozzles, the distribution system delivering the decontaminant solution to the nozzles and receiving sprayed decontaminant solution from the chamber;

a valve reprocessor connected with the fluid distribution system, for receiving an endoscope valve, the reprocessor opening the valve while flowing the solution over and through the valve;

a pump, connected with the fluid distribution system which pumps the decontaminant solution to the nozzles and valve reprocessor; and a control system which controls the delivery of the decontaminant solution to the nozzles and valve reprocessor.

13. A system for cleaning and microbially decontaminating an endoscope, the system comprising:
   a chamber for receiving the endoscope, the chamber including:
      stationary rear, two opposed side, and top panels and an open front adjacent the side panels that is closed by an access door, the side panels being spaced by greater than a minimum bend diameter of the endoscope;
      a rack supported by the rear panel and configured to support the endoscope in a coiled configuration on a plurality of pegs;
   a source of a microbial decontaminant solution;
   spray nozzles, disposed within the chamber, for spraying the decontaminant solution over an external surface of the endoscope, the spray nozzles including a plurality of nozzles mounted to the side panels and at least one of the door and rear panels for spraying the endoscope with focused sprays from a multiplicity of directions;
   at least one connection port disposed within the chamber for supplying the decontaminant solution to the internal passage;
   a fluid distribution system connecting the source of the decontaminant solution, the chamber, and the nozzles and connection port, the distribution system delivering the decontaminant solution to the nozzles and connection port and receiving sprayed decontaminant solution from the chamber;
   a pump, connected with the fluid distribution system which pumps the decontaminant solution to the nozzles and connection port; and
   a control system which controls the delivery of the decontaminant solution to the nozzles and connection port.

14. The system of claim 13, wherein the control system controls delivery to the nozzles such that nozzles whose spray patterns cross and would interfere with each other are operated alternately.

15. The system of claim 13, wherein the chamber defines a sump at the bottom thereof, the delivery system being connected with the sump for recirculating liquids that drain from the exterior and internal passages of the endoscope and collect in the sump.

16. A method of cleaning and microbially decontaminating a flexible endoscope having at least one internal passage comprising:
   a) coiling an endoscope on a rack and hanging the rack vertically within a chamber;
   b) placing a valve of the endoscope in a valve reprocessor within the chamber;
   c) spraying a washing solution over the endoscope from nozzles within the chamber to remove soil from exterior surfaces of the endoscope, the washing solution draining from the endoscope and collecting in the chamber below the endoscope;
   d) delivering the washing solution to the internal passage of the endoscope to remove soil from the internal passage of the endoscope, the washing solution coursing through the internal passage and draining into the chamber below the endoscope;
   e) spraying a microbial decontaminant solution over the endoscope from nozzles within the chamber to microbially decontaminate the exterior surfaces of the endoscope;
   f) delivering the microbial decontaminant solution to the internal passage of the endoscope to microbially decontaminate the internal passage of the endoscope; and
   g) delivering the microbial decontaminant solution to the valve reprocessor, the reprocessor opening the valve while the microbial decontaminant solution flows over and through the valve.

17. The method of claim 16, wherein step a) includes:
   positioning the endoscope within the chamber such that spray jets of the washing solution and the microbial decontaminant solution from the nozzles impinge on exterior surfaces of the endoscope during steps b)and d), each of the exterior surfaces of the device being contacted with at least one spray jet at an angle of no more than 45 degrees from perpendicular to the endoscope.

18. A method of cleaning and microbially decontaminating a flexible endoscope having at least one internal passage comprising:
   a) coiling the flexible endoscope around a rack and releasably coupling a tip portion of the endoscope to one of the rack and another portion of the endoscope with an endoscope clip to keep the tip portion securely positioned;
   b) positioning the rack and the endoscope within a chamber;
   c) spraying a washing solution over the endoscope from nozzles to remove soil from exterior surfaces of the endoscope;
   d) delivering the washing solution to the internal passage of the endoscope to remove soil from the internal passage of the endoscope;
   e) spraying a microbial decontaminant solution over the endoscope from nozzles within the chamber to microbially decontaminate the exterior surfaces of the endoscope;
   f) delivering the microbial decontaminant solution to the internal passage of the endoscope to microbially decontaminate the internal passage of the endoscope; and
   g) delivering the microbial decontaminant solution to an internal fluid path in the clip, the solution passing through apertures in the clip to contact the endoscope, spray jets of the washing solution and the microbial decontaminant solution from the nozzles impinging on exterior surfaces of the endoscope during steps c)and e).

19. The method of claim 18, wherein the step of positioning the endoscope includes:
   mounting the endoscope on the rack and positioning the rack mounted endoscope in the chamber.

20. The method of claim 19, wherein the device is an endoscope and the step of mounting the device on the rack includes:
   coiling the endoscope on the rack.

21. The method of claim 20, further including after a microbial decontamination cycle:
   lifting the rack from the chamber to remove the rack and the endoscope as a unit.

22. A method of cleaning and microbially decontaminating a device having at least one internal passage comprising:
   a) positioning the device within a chamber;
   b) spraying a washing solution over the device from nozzles within the chamber to remove soil from exterior surfaces of the device;
   c) delivering the washing solution to the internal passage of the device to remove soil from the internal passage of the device;

d) spraying a microbial decontaminant solution over the device from nozzles within the chamber to microbially decontaminate the exterior surfaces of the device;

e) delivering the microbial decontaminant solution to the internal passage of the device to microbially decontaminate the internal passage of the device; and during steps b) and d):

pulsing at least two sets of the nozzles in sequence such that the device is impacted by spray jets from one set of nozzles for a first period of time and is then impacted by spray jets from another set of nozzles for a second period of time, the pulsing causing the device to wobble, changing points of contact of the device.

23. A method of cleaning and microbially decontaminating a device having internal passages comprising:

a) positioning the device within a chamber;

b) spraying a washing solution over the device from nozzles within the chamber to remove soil from exterior surfaces of the device;

c) supplying the washing solution to a first internal passage of the device at a first washing solution pressure;

d) supplying the washing solution to a second internal passage of the device at a second washing solution pressure, different from the first washing solution pressure;

e) spraying a microbial decontaminant solution over the device from nozzles within the chamber to microbially decontaminate the exterior surfaces of the device;

f) supplying the decontaminant solution to the first internal passage at a first decontaminant solution pressure;

g) supplying the decontaminant solution to the second internal passage at a second decontaminant solution pressure, different from the first decontaminant solution pressure.

24. The method of claim 22, further including:

controlling steps b), c), d), e) with a computer control system.

25. The method of claim 24, wherein the control system asynchronously controls steps b), c), d), and e) in at least one additional chamber.

26. The method of claim 22, further including, prior to steps d) and e):

spraying a pretreatment solution over the device which includes a buffering agent and a corrosion inhibitor.

27. The method of claim 22, further including, after step e):

spraying a sterile rinse water from nozzles within the chamber over exterior surfaces of the device; and delivering sterile rinse water to the internal passage of the device.

28. The method of claim 22, further including, after step e):

blowing air from nozzles within the chamber over exterior surfaces of the device; and delivering air to the internal passage of the device.

* * * * *